(12) United States Patent
Lee et al.

(10) Patent No.: US 7,356,175 B2
(45) Date of Patent: Apr. 8, 2008

(54) IDENTIFYING DEFECTS IN DECORATIVE WOOD PANELS

(75) Inventors: Michael Lee, Danville, VA (US); Steve Pung, Black Mountain, NC (US); Vidar Solli, Kongsberg (NO); Sigmund Sundfor, Kongsberg (NO)

(73) Assignee: Columbia Forest Products, Inc., Portland, OR (US)

( * ) Notice: Subject to any disclaimer, the term of this patent is extended or adjusted under 35 U.S.C. 154(b) by 738 days.

(21) Appl. No.: 10/671,861

(22) Filed: Sep. 25, 2003

(65) Prior Publication Data

US 2005/0147286 A1 Jul. 7, 2005

(51) Int. Cl.
*G06K 9/00* (2006.01)
*B07C 5/14* (2006.01)
(52) U.S. Cl. ...................................... 382/141; 209/517
(58) Field of Classification Search ..................... None
See application file for complete search history.

(56) References Cited

U.S. PATENT DOCUMENTS

| 5,544,256 | A | * | 8/1996 | Brecher et al. | ............. 382/149 |
| 6,148,099 | A | * | 11/2000 | Lee et al. | ................... 382/149 |
| 6,336,086 | B1 | * | 1/2002 | Perez et al. | ................... 703/13 |
| 2002/0085093 | A1 | * | 7/2002 | Frigon et al. | ................. 348/91 |

* cited by examiner

*Primary Examiner*—Matthew C. Bella
*Assistant Examiner*—Alex Liew
(74) *Attorney, Agent, or Firm*—Schwabe, Williamson & Wyatt, P.C.

(57) ABSTRACT

A scanning system which scans for defects in decorative panels by generating images of the panels. A comparative program, i.e., recipes of samples of decorative panels having defect types and degrees, enables the system to make comparisons of defects and through said comparisons to grade the defects whereby the panels are graded as, e.g., acceptable, re-work, shop or reject. The program is modified for different decorative wood species and a controller dictates the comparative program to be applied for different customer orders of decorative wood panels.

5 Claims, 5 Drawing Sheets

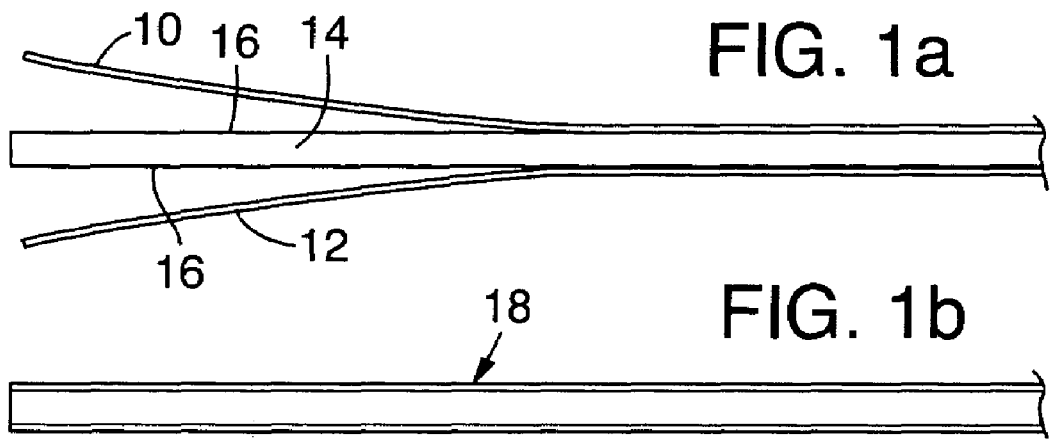
FIG. 1a
FIG. 1b
FIG. 1c
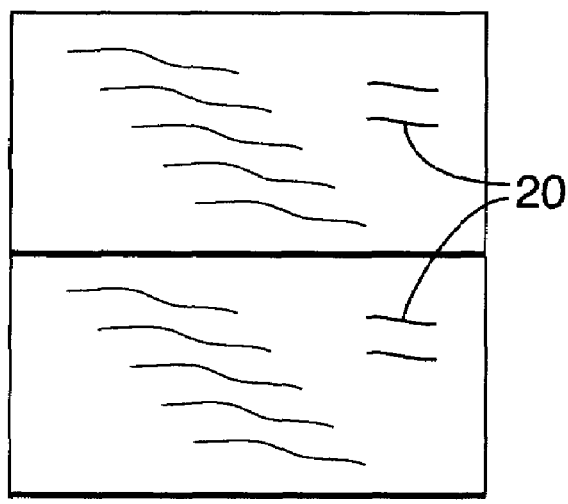
FIG. 1d
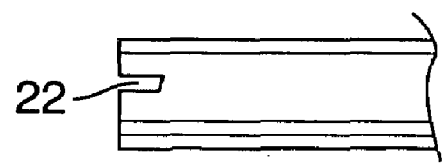
FIG. 1e
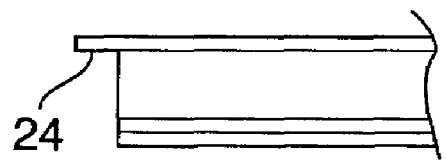
FIG. 1f
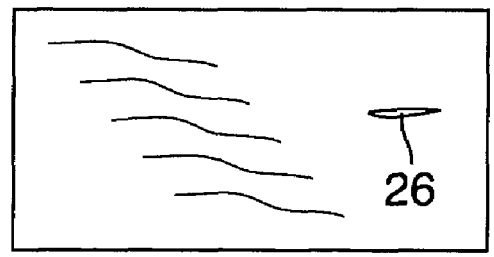

IDENTIFYING DEFECTS IN DECORATIVE WOOD PANELS

FIELD OF THE INVENTION

This invention relates to an automatic classification system that classifies defects and natural wood shading that are common to and the result of manufacturing decorative wood panels.

BACKGROUND OF THE INVENTION

Whereas most decorative wood facing is produced from hardwood, there are decorative wood types that are not truly hardwood. Reference herein to decorative hardwood is intended to encompass also decorative wood panels that are not truly hardwood.

Decorative wood panels, e.g., hardwood plywood panels, are used as decorative facings for cabinetry, furniture and the like. It is attractive in its natural hardwood shading. It has no repetitive pattern in the manner by which it is shaded and a part of its attractiveness is embodied in the unique shading of each hardwood facing.

Yet, defects are visually recognizable as distinguishable from the shading and are to be avoided. Whereas defective plywood facing is rejected prior to assembly of the facing sheets onto plywood, the assembly process itself can and does produce defects. These range from indentations to scratches to misaligned edges to thickness variations and so on.

Heretofore, such defects have been detected by visual inspection. However, the sheets are produced at a speed that makes visual inspection very difficult and it is estimated that 10% or higher of the defects are missed at the time of final inspection at the factory. The overlooked defective sheets are sent to customers who may well, at least partially, and/or occasionally produce an end product before the defect is discovered. Customers place high priority on obtaining defect-free decorative panels and it is accordingly highly desirable to detect defects following plywood assembly and before shipping them to a customer. Because visual detection is not satisfactory, it is desirable to develop an automatic system to detect such defects.

Scanning systems have been available for a number of years and are commonly used in the lumber producing industry and even in the subcategory of plywood production. A known system of defect detection has been developed, e.g., by the company Argos which is based on imagery or photography. Light is directed onto a subject from varying angles, and images are conveyed to a computer which detects shade differences that in turn identify defects. The system uses "detectors" and "classifiers" that first identify shade differences and then determines the extent of those differences. However, this system and all known prior systems have not been applied to the classification of production defects as may occur in the production of decorative e.g. hardwood plywood panels.

BRIEF DESCRIPTION OF THE INVENTION

It was determined that any form of defect that is visible manually, could similarly be made detectable photographically. Even indentations on the face of a decorative wood panel, through the appropriate direction of light directed onto or across the face of the panel, will appear photographically and thus is detectable. The natural shading of the decorative wood, commonly hardwood, is also photographically detected as a defect. However, the system can be programmed to determine that such form of defect is "acceptable." For the non-acceptable types of defects, the imagery is distinguishable as to defect type and defect severity and the system can be programmed to identify such defects and to apply grading thereto which enables sorting of that particular hardwood type by grade, e.g., acceptable, rework, shop, reject, etc.

Having determined that photography can be used to automatically detect defects, e.g., in decorative hardwood plywood panels, the challenge was to make such use feasible. Such feasibility was investigated by creating a system that will work for a single type of hardwood. The first requirement is to identify substantially every defect that typically results during the assembly process and which will impact on the acceptability of the product. The next requirement is establishing parameters that will enable grading of those defects.

Whereas such grading was previously done by judgment calls based on visual observation by graders, it was determined necessary to apply a computer recognizable grading system. This was accomplished by denoting the computer readout, e.g., the total of the defect as defined by pixels, for sample panels of known grade types. The computer is then "taught" that such readouts indicate the different grade levels, e.g., rework, shop, reject, etc. This same process was repeated over and over for each type of defect that affects acceptability and non-acceptability and the grading there between. Upon completion as to that selected type of decorative hardwood plywood, the photographic scanning could then be made adaptable to the inspection and grading of that decorative plywood type.

The problem next encountered was how the concept could be adapted to the typical decorative hardwood plywood manufacturer who produces a variety of different types of decorative hardwood plywood on the same assembly line. Even more of a problem is that such manufacturers produce product based on customer orders and it is not feasible to develop independent recipes for every conceivable product type.

For the most part, the repetitive type of orders can be resolved by repeating the above process for each of the common types of decorative hardwood panel orders thereby generating a multiple of cooperative instructive programs (parameters) herein generally referred to as recipes. The manner of converting between the different product types; i.e., different hardwood faces, is a matter of programming the detectors/classifiers to shift between the different recipes available. This conversion for the preferred embodiment of the present invention is accomplished by a controller that interfaces with customers' production order and the scanning system's computer. For example, the different orders are applied to a work order form that identifies each product type using a bar code. The controller is equipped with a bar code reader that identifies which of the recipes are appropriate for that order, and directs the computer to make the appropriate conversion.

The second part of the problem is the customization of the system to non-typical product orders. The controller is provided with the capability of selecting individual ones of the instructive programs as applied to traditional product orders where there are similar visual characteristics. The computer is responsive to such selection to effectively generate a new recipe for that non-typical product order. In such cases the new recipe can then be classified as a typical recipe to be used for future orders.

In summary, the present invention improves on those basic capabilities of prior known photographic scanning. The classifier is utilized in part to generate acceptance for natural or desired "defects;" e.g., the natural shading of a hardwood face. The system is further enhanced by the incorporation of numerous detector/classifier systems (recipes) to accommodate a wide variety of visual defects as may result from the different operations involved in decorative panel production. A secondary aspect of the invention is the provision of a controller that enables conversion between different recipes for different hardwood types and additionally still, the provision of customization resulting from selectively combining different ones of the instructive programs of existing recipes.

The invention will be more fully understood and appreciated upon reference to the following detailed description and accompanied drawings.

BRIEF DESCRIPTION OF THE DRAWINGS

FIG. 1a-f are views illustrating schematically the process of assembling a decorative plywood panel and examples of defects that can occur during such assembly;

DETAILED DESCRIPTION OF A PREFERRED EMBODIMENT

Figure 2:
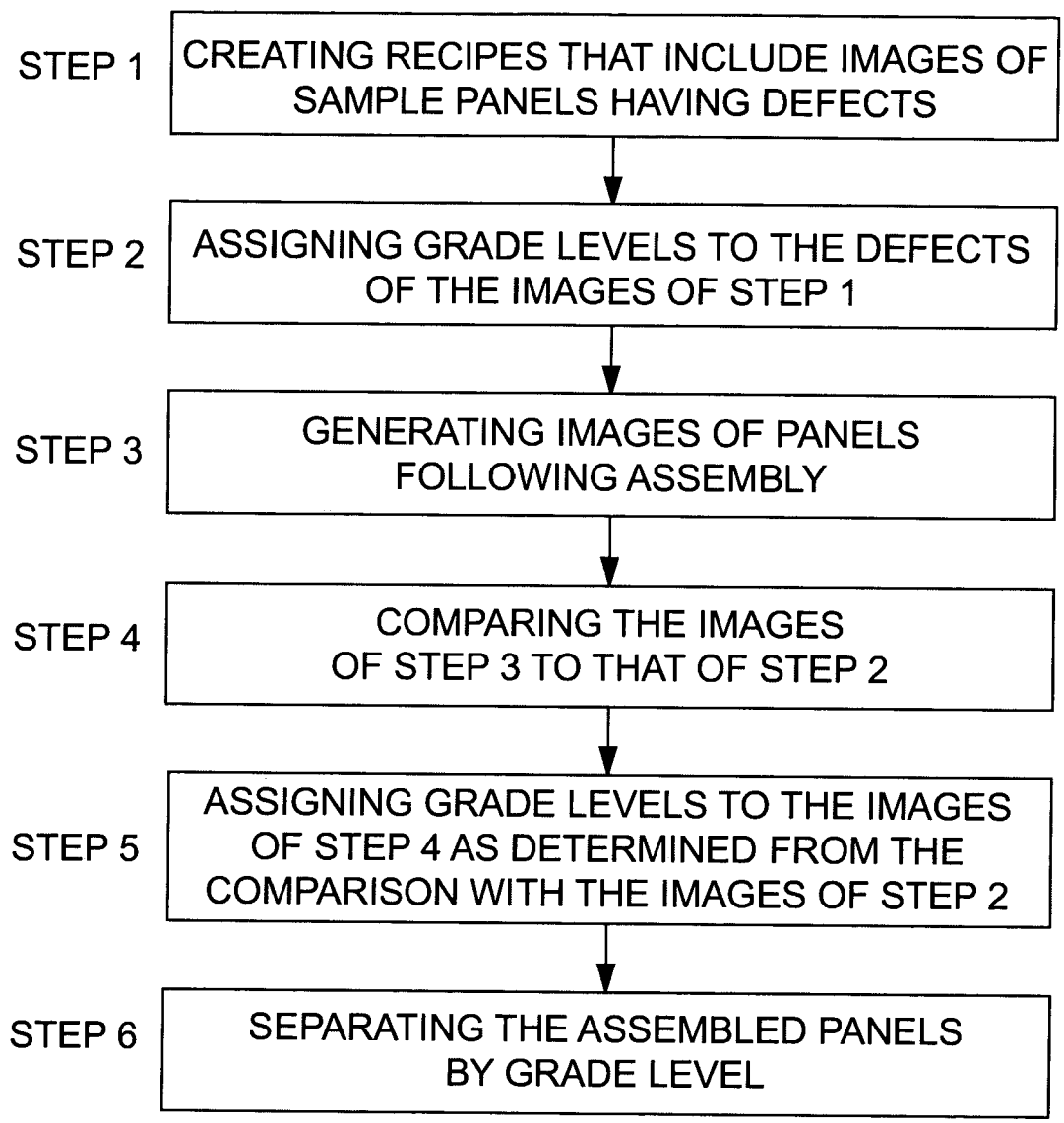
FIG. 2 is a flow chart of the scanning operation as incorporated into an embodiment of the invention.

As a first step to explaining/describing a preferred embodiment of the invention, reference is made to the production process of FIG. 1a through FIG. 1f. With reference first to FIG. 1a, it will be appreciated that decorative laminates 10 and 12 are adhered (e.g., by adhesive 16) to a plywood core or blank 14. Various material types for the blank include particle board and multi-directional fiber board as well as laminate plywood sheets, but it is to be understood that this invention is not limited to any particular type of blank or core. The blank or core 14 has opposed sides that are flat and substantially free of surface irregularities. The facing sheets 10 and 12 are very thin, e.g., 0.6 mm., and such surface irregularities may show through to the surface of the facing and are to be avoided.

Whereas the facing sheets 10, 12 are also pre-selected to be defect-free, should the lay up process represented by FIG. 1a be carried out to perfection, there would be no requirement for follow up inspection. Because such perfection does not exist, the process of applying and adhering the facing sheets 10, 12 to the core 14 generates an appreciable number of defects. Core and facing sheets travel through a plurality of lay up operations such as removing the sheets and core from stacks or bins, applying glue, merging the sheets with the core or blank, applying appropriate pressure and heat to cause curing and bonding of the sheets to the core, etc. Each of such operations can and do produce defects.

Through experience with this process, the manufacturer knows the types of unacceptable defects that are generated by the manufacturing process. However, even though the types of manufacturing defects are known and inspectors can be trained to look for such defects, the speed of production renders it difficult for inspectors to detect such defects.

The first step in automating the inspection in accordance with a preferred embodiment of the invention is to catalogue the types of defects that occur during the manufacturing operation. Examples are: scratches 20 as shown in FIG. 1c, e.g., caused by hard particles becoming deposited on a press roller; edge nicks or gouges 22 as illustrated in FIG. 1d, e.g., caused by a loose particle at the core edge not previously noticed but which is dislodged from the core during the assembly process; misalignment of the face of sheet and core as indicated by reference 24 in FIG. 1e; and e.g., a previously unnoticed surface crack 26 that is expanded to a visible state by heat that is applied during curing of the adhesive 16, etc.

As a second step, there is established for each defect type a range of acceptability. The defect may e.g. be so slight as to be fully acceptable; not acceptable as is but qualified for re-work; not acceptable as is and not qualified for re-work, i.e. shop; and not acceptable i.e. rejected. Such is typically a judgment call by person inspectors. This judgment call is converted to an absolute utilizing measurement techniques as applied to the images that are identified by the photographic scanner. Such measurements are converted to numerical values, e.g., 0.0 to 0.25 being considered acceptable, 0.25 to 0.50 being considered re-work grade, 0.50 to 0.75 being considered as shop grade, and 0.75 to 1.0 being considered as reject grade.

In order to convey this information to the automated inspection system, hundreds or even thousands of plywood samples are photographed, e.g., by a line scan camera (see FIG. 3), and each sample is categorized as being of a particular defect type (scratch, edge nick or gouge, misalignment, split, etc.) and then graded by, e.g., (0.0 to 1.0).

The above process is repeated for each of a plurality of typical species of wood (primarily but not exclusively hard woods) used as decorative panel facings. Upon completing this task, the next step is to marry the information to the scanning system.

The scanning system includes defect detectors and defect classifiers. There is a detector and a classifier for each of the different types of defects. For each of the detectors and classifiers, there is a grading recipe including parameters of acceptability as determined for the images from the photographed samples. Grading is a process of measurement, e.g., of pixels generated by the defect image and converted to bitmap imagery. Because the computer has been "taught" as to what measurements indicate the different grade types, each defect can accordingly be graded. As the decorative sheets come off the assembly line, each sheet in turn is scanned and the defect detector first identifies the existence of a particular type of defect and upon detection, a defect classifier determines a grade for that defect. A control responds to such grade determination to divert the flow path of the sheet into the respective storage bins. The above description is represented diagrammatically in the six-step flow chart of FIG. 2.

As previously explained, each species of wood has a customized detection system referred to as grading recipes. As also previously explained, the decorative sheets include natural wood shading. As concerns a particular specie of wood facing, e.g., birch, oak, maple, cherry, etc., the detector/classifiers need to be reprogrammed with the compatible recipes.

The identity of the specie type and accordingly the desired recipe setting is the task of a controller. A controller is provided with the input as to specie and other criteria via customer order. Thus a customer order may be provided as a bar code readable by the controller and the controller identifies the specie type, the number of pieces to be processed, and this information, and such other information as required to set the stage for inspection is conveyed to the scanning system.

Operational Review

1. For each of the plurality of species of decorative panels, sample sheets having each type of defect for that specie are photographed and parameters of acceptability are determined.

2. A bar code from a customer order is input into a controller and the controller identifies the specie type to the scanner.

3. Each assembled sheet is passed through a line scan camera, an image is generated, and from that image, defects are detected.

4. The different defects as may be found on a sheet are independently graded by classifiers using the parameter settings of Step 1, and from that grading and based on a worst case grade identity, each such sheet is determined to be acceptable, re-work, shop or reject. Mechanical deflectors are operated accordingly to direct each sheet into, e.g., holding bins of common grade. Alternatively, the sheets may be marked with a grade identification and separated by grade in a subsequent operation.

The system as generally described above is schematically illustrated in FIG. 3 which is now referred to. A decorative panel type is identified by a customer order and the appropriate grading recipes are activated by input from control 50. A decorative panel/sheet 30, e.g., previously assembled in a manufacturing process (FIG. 1*a*) is illuminated by a light source 32 as the panel 30 passes under a line scan camera 34. The images (pixels) are conveyed to a dual processor PC (programmable computer) 36. A frame grabber 38 within the PC 36 converts the pixels to bit map images which are conveyed to defect detectors 40. The defect detectors through image evaluation, enabled by established parameters as stored in the grading recipes memory 44, identify any defective panels and the type of defect, and then they are graded using the classifier parameters (also from grading recipes 44). The combination of defects are accumulated at grading station 46 where that panel 30 is assigned to a particular grading bin (acceptable, re-work, shop and reject), i.e., the control signal generated at station 48.

As concerns the various components of the above example of a scanning system of the invention, the lighting 32 is known technology and requires no further explanation within this art. The digital line scan camera 34 is a standard industrial line scan camera having a resolution approximately 0.5 mm×0.5 mm. An electronic and programmable shutter (also known and available) is used to adapt to different wood species. The use of linescan cameras in web inspection application is known technology and requires no further explanation. The dual processor 36 is preferably a multi-processor PC.

The frame grabber 38 again is a commercially available unit known to the art. The purpose of the frame grabber is to convert the signals from the digital line scan camera to a bit map image that is accessible from a program running on the PC.

The defect detectors 40 is a set of software algorithms that looks for certain properties such as spots, cracks, broken corners, etc. The algorithms used are well known to image processing algorithms and use contrast variation, intensity, shape and position to identify atypical properties in the surfaces. Each detector produces a number that indicates the quantity of a defect, the total area covered by a defect or its length if it is a split or crack.

Figure 3:
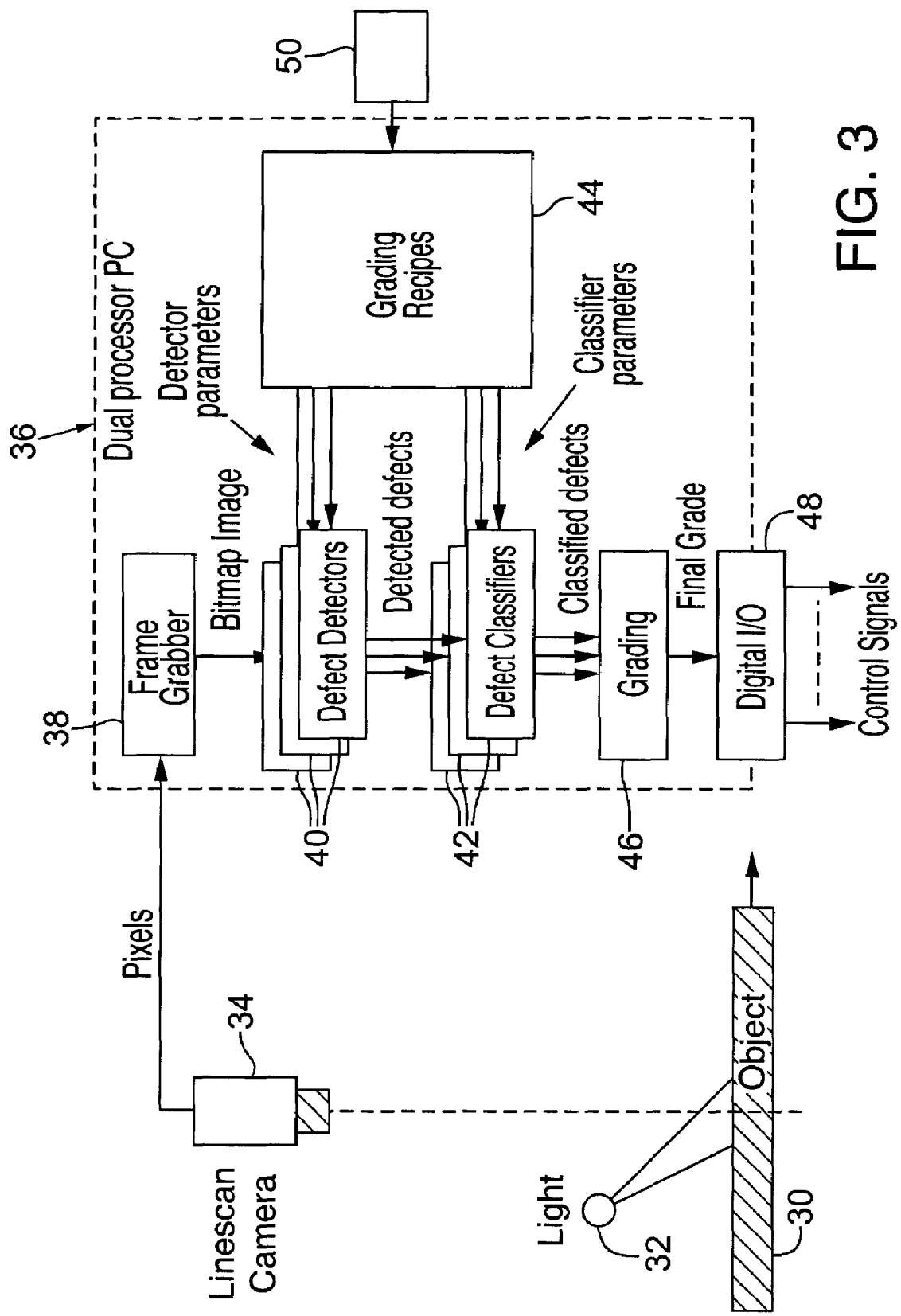
FIG. 3 is a flow chart illustrating a scanning operation and grading procedure of an embodiment of the invention.

The grading recipes 44 are of two types as indicated by the arrows of FIG. 3 (one set of arrows directed to the defect detectors 40 and another set to the defect classifiers 42). Detection recipes are desirable due to the large variation in properties for the different species. The parameters controlling the detectors are tailored to each specie. Parameters that are changed are e.g. threshold levels for spot detection, minimum size for spots, acceptable levels of roughness, etc. Properties that influence the detector settings include e.g. species: birch, oak, maple, cherry, etc.; cut: rotary, whole piece, rotary spliced, plain spliced, etc.; type: heart or sap; core: veneer core, particle board core, MDF core, etc. All or only a set of these parameters identifies a detector recipe. For some products the detector setting can be the same dependent on the way a laminate is cut. In such case, the cut identification may be omitted in the detector recipe identifier.

The parameters are a part of the product specification received from plant information (production order when initiating a product run). The detector recipe that best matches the product specification is selected. It is therefore not necessary that a detector recipe be provided for each individual product run. However, products may have different veneer and different grading requirements for top and bottom surfaces of the plywood sheets (see FIG. 1*b*). The customer order input, in such cases will specify the parameters for both surfaces.

Classification recipes contain information about which defects to take into consideration and the acceptance level for the different grades. There is a set of parameters for each identifiable defect (corresponding to the defect detectors).

Figure 4:
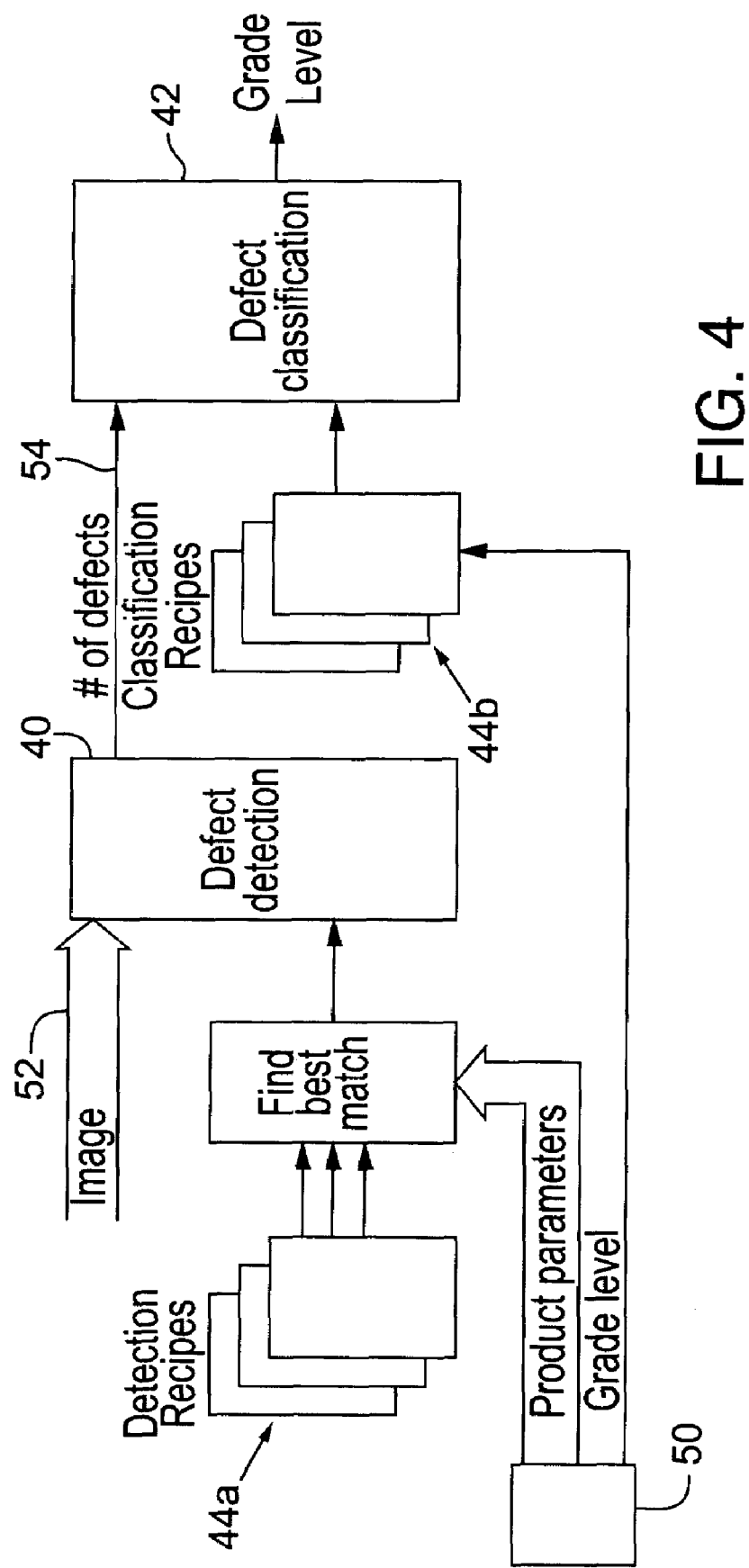
FIG. 4 is an information flow diagram within the operation illustrated in FIG. 3.

FIG. 4 illustrates the flow of information through the processor 36. The product parameters and grade level as provided to the computer from the controller 50 is first used to find a best match and accordingly determine which of the recipes will be applied. The image 52 from frame grabber 38 is conveyed to the defect detector 40 which identifies the different defects of that image and conveys that information to the defect classifier 42 as indicated by arrow 54. The acceptable grade level from controller 50 is entered into the classification recipes indicated by arrow 56 and the information is provided to the defect classifier 42. The recipe parameters are stored in registry and each recipe has its own key with sub keys for each defect type. Accordingly, a grade level is applied to the sheet from which the image was obtained and as explained and illustrated in FIG. 2, the sheet of that image is diverted as it leaves the scan area of FIG. 2 to the appropriate storage bin.

Figure 5:
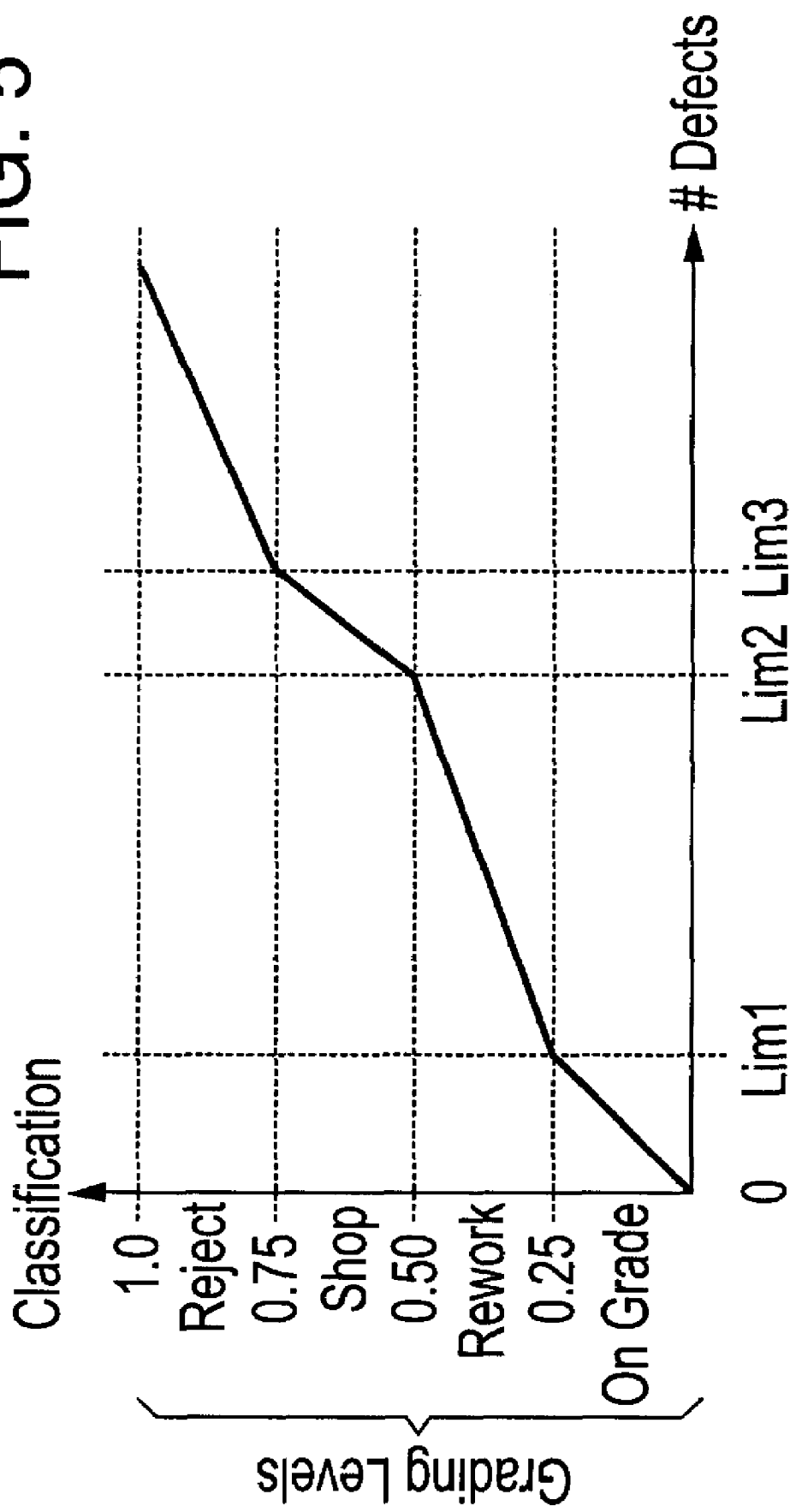
FIG. 5 is a chart illustrating a grading process as may be used in the operation illustrated in FIG. 3.

FIG. 5 is a defect classification chart that illustrates the defect classification process for a single defect classifier. In this example, defects are graded using the number system from 0.0 (no defects) to 1.0. Limits are set (based on the comparison with samples). A scanned sheet that has a grade of less than 0.25 is graded acceptable whereas above 0.25 e.g., between 0.25 and 1.0 is graded "re-work," "shop," or "reject." As concerns a single sheet having multiple defects, the same process is repeated for each of such multiple defects, and the final grade given to that sheet is the one that has been graded with the highest number. When the final grading is decided, the system outputs a "high" on the associated digital output to direct the sheet to the appropriate bin.

Whereas the above provides a disclosure of the preferred embodiment of the invention, it will be understood that numerous modifications, variations and/or improvements may be made by those skilled in the art without departing from the scope of the invention as defined by the claims appended hereto.

What is claimed is:

1. An inspection system for automatically detecting and classifying manufacturing defects in decorative wood panels following assembly of a decorative wood laminate, having a decorative wood facing, to a core or blank, said decorative wood facing having desirable areas of natural wood shading and said system using a photographic image of said panel as the basis for detecting and classifying said defects, which system comprises:

creating multiple sets of computer driven recipes corresponding to multiple decorative wood panel types, each computer drive recipe utilizing detectors and classifiers specifically created from images of defects of varying types and degrees exhibited by sample decorative wood panels of a corresponding decorative wood panel type comparable to said decorative wood panels to be inspected;

providing a controller for instructing the system as to which decorative wood panel type is to be processed and accordingly the recipes to be applied to that wood panel type, the controller further comprising the capability of examining the detectors and classifiers of the various recipes, determining similarities of wood type defects of such various recipes as compared to a decorative wood panel type for which a recipe is not created, and selecting desired ones of said detectors and classifiers for custom creating a new recipe for said decorative wood type;

providing a work order form which identifies production criteria including a decorative wood panel type to be produced, such identification in the form of a bar code readable by the controller and transferable by the controller to the computer driven recipes for selection of the applicable recipe;

photographically scanning said decorative wood panels to be inspected following assembly and determining therefrom and with reference to the applied recipes the occurrence of defects and a defect value based on the size and shape of the defect; and assigning a grade of acceptability to such inspected panels based upon the defect value indicated.

2. A system as defined in claim 1 which includes selectively diverting said panels into segregated receiving stations based on a common grade of acceptability.

3. A system for detecting and classifying defects in decorative wood panels having decorative wood shading following assembly of decorative wood laminates to cores in the production of the panels, wherein each decorative wood panel includes a decorative wood laminates at opposed sides of said decorative wood panel, said system comprising:

creating recipes having value identifiers or parameters using photographic images of sample decorative wood panels exhibiting different types of defects and different degrees of the defects within the different types of defects;

assigning different grade levels to the different value identifiers for determining acceptability of the panels as assembled and specifically determining as acceptable the natural wood shading of said panels, said assignment of grade levels applicable to the two sides independently;

photographically scanning both sides of the decorative wood panels following assembly thereof and thereby producing dual images for each panel;

identifying defects and values of said defects determined by said recipes to first determine a type of defect and, second, to determine a degree of that defect;

classifying the panels as assembled into said grades of acceptability; and providing for separation of the assembled panels by grade of acceptability.

4. A system as defined in claim 3 wherein each defect is assigned a grade level having multiple levels of acceptability from best to poorest, and said system further including a step whereby assembled panels having multiple defects are assigned different grade levels and a final grade as determined by the defect receiving the poorest grade level.

5. A system as defined in claim 4 having multiple recipes for multiple types of decorative wood panels, and including a controller receiving instructions as to processing of different types of decorative wood panels and said controller instructing the system as to the recipe to be utilized.

* * * * *